US006851949B1

(12) United States Patent
Sachdeva et al.

(10) Patent No.: US 6,851,949 B1
(45) Date of Patent: *Feb. 8, 2005

(54) METHOD AND APPARATUS FOR GENERATING A DESIRED THREE-DIMENSIONAL DIGITAL MODEL OF AN ORTHODONTIC STRUCTURE

(75) Inventors: Rohit Sachdeva, Plano, TX (US); Rüdger Rubbert, Berlin (DE)

(73) Assignee: OraMetrix, Inc., Richardson, TX (US)

( * ) Notice: Subject to any disclaimer, the term of this patent is extended or adjusted under 35 U.S.C. 154(b) by 0 days.

This patent is subject to a terminal disclaimer.

(21) Appl. No.: 09/560,134

(22) Filed: Apr. 28, 2000

(Under 37 CFR 1.47)

Related U.S. Application Data

(63) Continuation-in-part of application No. 09/452,031, filed on Nov. 30, 1999, now Pat. No. 6,431,870.

(51) Int. Cl.[7] .............................................. A61C 11/00

(52) U.S. Cl. ...................................... 433/213; 433/24

(58) Field of Search ............................ 433/6, 24, 213, 433/214, 229

(56) References Cited

U.S. PATENT DOCUMENTS

| 4,575,805 | A | 3/1986 | Moermann et al. |
| 4,742,464 | A | 5/1988 | Duret et al. ............... 364/474 |
| 5,011,405 | A | 4/1991 | Lemchen |
| 5,027,281 | A | 6/1991 | Rekow et al. ......... 364/474.24 |
| 5,238,404 | A | 8/1993 | Andreiko |
| 5,338,198 | A | 8/1994 | Wu et al. ................... 433/213 |
| 5,368,478 | A | 11/1994 | Andreiko et al. |
| 5,395,238 | A | 3/1995 | Andreiko et al. |
| 5,431,562 | A | 7/1995 | Andreiko et al. |
| 5,447,432 | A | 9/1995 | Andreiko et al. |
| 5,454,717 | A | 10/1995 | Andreiko et al. |
| 5,456,600 | A | 10/1995 | Andreiko et al. |
| 5,464,349 | A | 11/1995 | Andreiko et al. |
| 5,474,448 | A | 12/1995 | Andreiko et al. |

(List continued on next page.)

OTHER PUBLICATIONS

Syrinx, Bending Robot.
Syrinx, Orthotherm.
Syrinx, 3D Scanner.
Dianne Rekow, M.S.M.E., D.D.S., "Computer–aided design and manufacturing in dentistry: A review of the state of the art", Journal of Prosthetic Dentistry, Volume 58, pp. 512–416 (Oct. 1987).
Co–pending U.S. Patent Application of Rohit Sachdeva, Ser. No. 09/452,031 filed Apr. 20, 2000.

*Primary Examiner*—Nicholas D. Lucchesi
(74) *Attorney, Agent, or Firm*—McDonnell Boehnen Hulbert & Berghoff

(57) ABSTRACT

A method and apparatus for generating a three-dimensional digital model of a desired orthodontic structure include processing that begins by obtaining a three-dimensional model of an actual orthodontic structure, wherein the three-dimensional digital model is defined in x, y, z space. The processing then continues by generating an interim three-dimensional model of the desired orthodontic structure less teeth. The interim three-dimensional model is designed in x, y, z space and includes the desired placement of an occlusal plane, an upper-arch form, a lower-arch form, an upper-arch midline, and a lower-arch midline. The processing then continues by positioning the upper and lower teeth with respect to the interim digital model and the defined x, y, z space to obtain a first pass three-dimensional digital model of the desired orthodontic structure. The processing continues by determining whether achieving the first pass three-dimensional model is feasible. When achieving the first pass three-dimensional image is feasible, the processing continues by utilizing the first pass three-dimensional model as the desired three-dimensional digital model.

28 Claims, 7 Drawing Sheets

U.S. PATENT DOCUMENTS

| | | |
|---|---|---|
| 5,518,397 A | 5/1996 | Andreiko et al. |
| 5,533,895 A | 7/1996 | Andreiko et al. |
| 5,542,842 A | 8/1996 | Andreiko et al. |
| 5,618,176 A | 4/1997 | Andreiko et al. |
| 5,879,158 A | 3/1999 | Doyle et al. ............... 433/24 |
| 5,975,893 A | 11/1999 | Chishti et al. ............... 433/6 |
| 6,068,482 A | 5/2000 | Snow ...................... 433/223 |
| 6,099,314 A | 8/2000 | Kopelman et al. ......... 433/213 |
| 6,217,325 B1 | 4/2001 | Chishti et al. ............... 433/24 |
| 6,227,850 B1 | 5/2001 | Chishti et al. ............... 433/24 |
| 6,227,851 B1 | 5/2001 | Chishti et al. ............... 433/24 |
| 6,431,870 B1 * | 8/2002 | Sachdeva .................. 433/24 |
| 6,616,444 B2 | 9/2003 | Andreiko et al. ............ 433/3 |
| 2002/0025503 A1 | 2/2002 | Chapoulaud et al. ....... 433/24 |
| 2002/0028417 A1 | 3/2002 | Chapoulaud et al. ....... 433/24 |

* cited by examiner 3D digital model of desired orthodontic structure
30

METHOD AND APPARATUS FOR GENERATING A DESIRED THREE-DIMENSIONAL DIGITAL MODEL OF AN ORTHODONTIC STRUCTURE

CROSS REFERENCE TO RELATED APPLICATION

This is a continuation-in-part of Ser. No. 09/452,031, filed Nov. 30, 1999 now U.S. Pat. No. 6,431,870.

TECHNICAL FIELD OF THE INVENTION

This invention relates generally to the practice of orthodontics and in particular to a method and apparatus for treating an orthodontic patient.

BACKGROUND OF THE INVENTION

Orthodontics is the practice of manipulating a patient's teeth to provide better function and appearance. In general, brackets are bonded to a patient's teeth and coupled together with an arched wire. The combination of the brackets and wire provide a force on the teeth causing them to move. Once the teeth have moved to a desired location and are held in a place for a certain period of time, the body adapts bone and tissue to maintain the teeth in the desired location. To further assist in retaining the teeth in the desired location, a patient may be fitted with a retainer.

To achieve tooth movement, orthodontists utilize their expertise to first determine a three-dimensional mental image of the patient's physical orthodontic structure and a three-dimensional mental image of a desired physical orthodontic structure for the patient, which may be assisted through the use of x-rays and/or models. Based on these mental images, the orthodontist further relies on his/her expertise to place the brackets and/or bands on the teeth and to manually bend (i.e., shape) wire, such that a force is asserted on the teeth to reposition the teeth into the desired physical orthodontic structure. As the teeth move towards the desired location, the orthodontist makes continual judgments as to the progress of the treatment, the next step in the treatment (e.g., new bend in the wire, reposition or replace brackets, is head gear required, etc.), and the success of the previous step.

In general, the orthodontist makes manual adjustments to the wire and/or replaces or repositions brackets based on his or her expert opinion. Unfortunately, in the oral environment, it is impossible for a human being to accurately develop a visual three-dimensional image of an orthodontic structure due to the limitations of human sight and the physical structure of a human mouth. In addition, it is humanly impossible to accurately estimate three-dimensional wire bends (with an accuracy within a few degrees) and to manually apply such bends to a wire. Further, it is humanly impossible to determine an ideal bracket location to achieve the desired orthodontic structure based on the mental images. It is also extremely difficult to manually place brackets in what is estimated to be the ideal location. Accordingly, orthodontic treatment is an iterative process requiring multiple wire changes, with the process success and speed being very much dependent on the orthodontist's motor skills and diagnostic expertise. As a result of multiple wire changes, patient discomfort is increased as well as the cost. As one would expect, the quality of care varies greatly from orthodontist to orthodontist as does the time to treat a patient.

As described, the practice of orthodontic is very much an art, relying on the expert opinions and judgments of the orthodontist. In an effort to shift the practice of orthodontic from an art to a science, many innovations have been developed. For example, U.S. Pat. No. 5,518,397 issued to Andreiko, et. al. provides a method of forming an orthodontic brace. Such a method includes obtaining a model of the teeth of a patient's mouth and a prescription of desired positioning of such teeth. The contour of the teeth of the patient's mouth is determined, from the model. Calculations of the contour and the desired positioning of the patient's teeth are then made to determine the geometry (e.g., grooves or slots) to be provided. Custom brackets including a special geometry are then created for receiving an arch wire to form an orthodontic brace system. Such geometry is intended to provide for the disposition of the arched wire on the bracket in a progressive curvature in a horizontal plane and a substantially linear configuration in a vertical plane. The geometry of the brackets is altered, (e.g., by cutting grooves into the brackets at individual positions and angles and with particular depth) in accordance with such calculations of the bracket geometry. In such a system, the brackets are customized to provide three-dimensional movement of the teeth, once the wire, which has a two dimensional shape (i.e., linear shape in the vertical plane and curvature in the horizontal plane), is applied to the brackets.

Other innovations relating to bracket and bracket placements have also been patented. For example, such patent innovations are disclosed in U.S. Pat. No. 5,618,716 entitled "Orthodontic Bracket and Ligature" a method of ligating arch wires to brackets, U.S. Pat. No. 5,011,405 "Entitled Method for Determining Orthodontic Bracket Placement," U.S. Pat. No. 5,395,238 entitled "Method of Forming Orthodontic Brace," and U.S. Pat. No. 5,533,895 entitled "Orthodontic Appliance and Group Standardize Brackets therefore and methods of making, assembling and using appliance to straighten teeth".

Unfortunately, the current innovations to change the practice of orthodontic from an art to a science have only made limited progress. This limit is due to, but not restricted to, the brackets being the focal point for orthodontic manipulation. By having the brackets as the focal point, placement of each bracket on a corresponding tooth is critical. Since each bracket includes a custom sized and positioned wire retaining groove, a misplacement of a bracket by a small amount (e.g., an error vector having a magnitude of millimeter or less and an angle of a few degrees or less) can cause a different force system (i.e., magnitude of movement and direction of movement) than the desired force system to be applied to the tooth. As such, the tooth will not be repositioned to the desired location.

Another issue with the brackets being the focal point is that once the brackets are placed on the teeth, they are generally fixed for the entire treatment. As such, if the treatment is not progressing as originally calculated, the orthodontist uses his or her expertise to make the appropriate changes. The treatment may not progress as originally calculated for several reasons. For example, misplacement of a bracket, misapplication of a bend in the wire, loss or attrition of a bracket, bonding failure, the patient falls outside of the "normal" patient model (e.g., poor growth, anatomical constraints, etc.), patient lack of cooperation in use of auxiliary appliance, etc. are factors in delayed treatment results. When one of these conditions arise, the orthodontist utilizes his or her expertise to apply manual bends to the wire to "correct" the errors in treatment. Thus, after the original scientific design of the brackets, the practice of the orthodontic converts back to an art for many patients for the remainder of the treatment.

Another issue with the brackets being the focal point is that customized brackets are expensive. A customized bracket is produced by milling a piece of metal (e.g., stainless steel, aluminum, ceramic, titanium, etc.) and tumble polishing the milled bracket. While the milling process is very accurate, some of the accuracy is lost by tumble polishing. Further accuracy is lost in that the placement of the brackets on the teeth and installation of the wire are imprecise operations. As is known, a slight misplacement of one bracket changes the force on multiple teeth and hinders treatment. To assist in the placement of the custom brackets, they are usually shipped to the orthodontist in an installation jig. Such an installation jig is also expensive. Thus, such scientific orthodontic treatment is expensive and has many inherent inaccuracies.

Therefore, a need exists for a method and apparatus that generates a three-dimensional digital model of an orthodontic structure such that a scientific approach to orthodontics is realized.

DETAILED DESCRIPTION OF A PREFERRED EMBODIMENT

Generally, the present invention provides a method and apparatus for generating a three-dimensional digital model of a desired orthodontic structure. Such a method and apparatus include processing that begins by obtaining a three-dimensional model of an actual orthodontic structure, wherein the three-dimensional digital model is defined in x, y, z space. The processing then continues by generating an interim three-dimensional model of the desired orthodontic structure less teeth. The interim three-dimensional model is designed in x, y, z space and includes the desired placement of an occlusal plane, an upper-arch form, a lower-arch form, an upper-arch midline, and a lower-arch midline. The processing then continues by positioning the upper and lower teeth with respect to the interim digital model and the defined x, y, z space to obtain a first pass three-dimensional digital model of the desired orthodontic structure. The processing continues by determining whether achieving the first pass three-dimensional model is feasible. In essence, the determination is based on treatment constraints and whether the desired orthodontic structure can be achieved from the actual orthodontic structure given such constraints. When achieving the first pass three-dimensional image is feasible, the processing continues by utilizing the first pass three-dimensional model as the desired three-dimensional digital model. With such a method and apparatus, automation of orthodontic treatment is realized thereby providing a scientific approach to practice of orthodontics.

Figure 1:
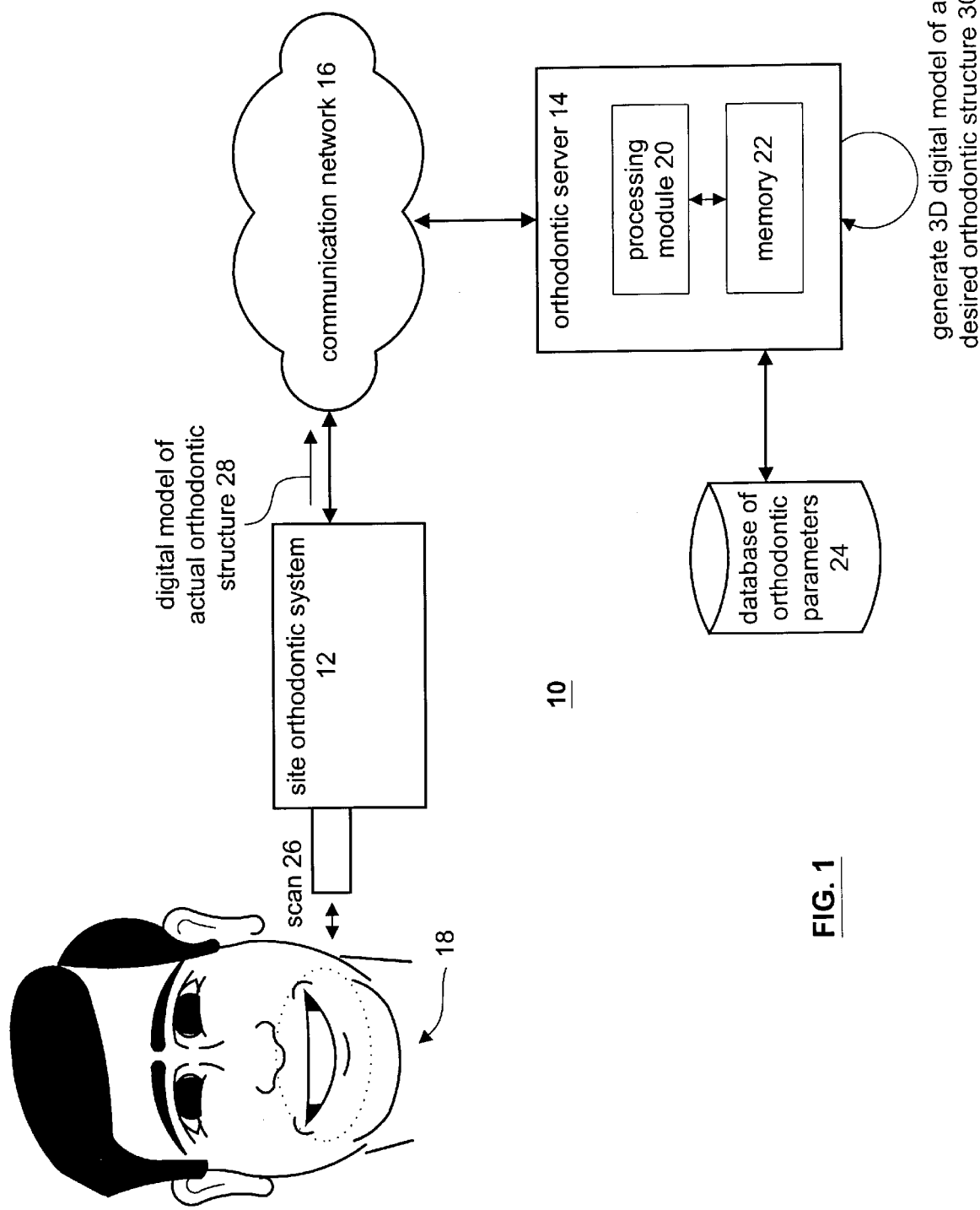
FIG. 1 illustrates a schematic block diagram of an orthodontic service system in accordance with the present invention.

The present invention can be more fully described with reference to FIGS. 1 through 7. FIG. 1 illustrates a schematic block diagram of an orthodontic servicing system 10 that includes a site orthodontic system 12, an orthodontic server 14, a communication network 16, and a database of orthodontic parameters 24. In operation, the site orthodontic system 12 scans 26 the patient's 18 orthodontic structure (i.e., teeth, gums, lips, upper and lower arches, and/or other facial features). The site orthodontic system 12 converts the scanned images of the orthodontic structure of the patient to produce a digital model of the actual orthodontic structure 28. The orthodontic server 14 receives the digital model of the actual orthodontic structure 28 via the communication network 16. The communication network 16 may be a direct connect, the Internet, local area network, wide area network, and/or any device that enables the transference of digital information from one computing type system to another.

The orthodontic server 14 includes a processing module 20 and memory 22. The processing module 20 may be a single processing device or a plurality of processing devices. Such a processing device may be a microprocessor, microcomputer, microcontroller, digital signal processor, central processing unit, state machine, logic circuitry, and/or any device that manipulates signals (e.g., analog and/or digital) based on operational instructions. The memory 22 may be a single memory device or a plurality of memory devices. Such a memory device may be a read-only memory, random access memory, floppy disk memory, hard drive memory, system memory, flash memory and/or any device that stores digital information. Note that when the processing module 20 implements one or more of its functions via a state machine or logic circuitry, the memory storing the corresponding operational instructions is embedded within the circuitry comprising the state machine or logic circuitry.

The orthodontic server 14 generates a three-dimensional digital model of the desired orthodontic structure 30 from the digital model of the actual orthodontic structure 28 and orthodontic parameters contained in the database of orthodontic parameters 24. To achieve this, the processing module 20, via operational instructions stored in memory 22, performs the processing steps of FIGS. 5 through 7, which will be discussed below. For a more detailed discussion for the site orthodontic system 12, the orthodontic server 14, and the database of orthodontic parameters 24 refer to co-pending patent application, which is hereby incorporated herein by reference, entitled METHOD AND APPARATUS FOR DETERMINING AND MONITORING ORTHODONTIC TREATMENT, Ser. No. 09/560,643; a co-pending patent application, which is hereby incorporated herein by reference, entitled METHOD AND APPARATUS FOR TREATING AN ORTHODONTIC PATIENT, Ser. No. 09/560,642; and a co-pending patent application, which is hereby incorporated herein by reference, entitled METHOD AND APPARATUS FOR SITE TREATMENT OF AN ORTHODONTIC PATIENT, Ser. No. 09/560,646 each having a filing date the same as the present patent application. Note that a specific embodiment of three-dimensional scanning used to generate the three-dimensional digital model is described in patent application 09/560,584 filed before the United States Patent Office on Apr. 28, 2000, entitled SYSTEM AND METHOD FOR MAPPING A SURFACE, and is hereby incorporated herein by reference.

Figure 2:
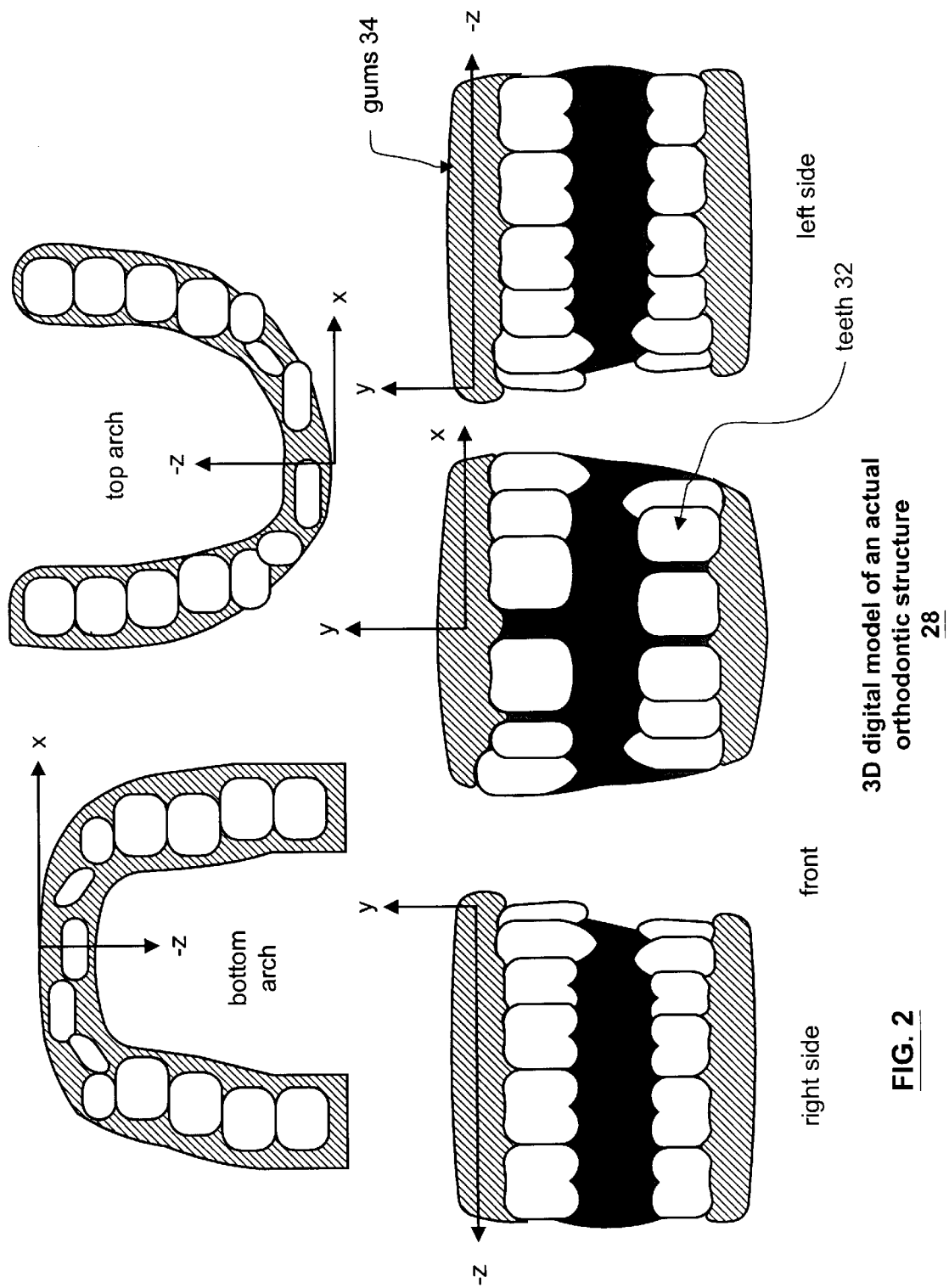
FIG. 2 illustrates a graphical representation of a three-dimensional digital model of an actual orthodontic structure in accordance with the present invention.

FIG. 2 illustrates a graphical representation of the three-dimensional digital model of an actual orthodontic structure 28. As shown, the orthodontic structure is mapped to x, y, z space. For a detailed discussion of the mapping of the digital model to x, y, z space refer to co-pending patent application, which is hereby incorporated herein by reference, entitled METHOD AND APPARATUS FOR PRODUCING A THREE-DIMENSIONAL DIGITAL MODEL OF AN ORTHODONTIC PATIENT, Ser. No 09/560,584, has a filing date the same as the present patent application and is assigned to the same assignee as the present patent application. As shown, the three-dimensional digital model of the actual orthodontic structure 28 includes surface images for the teeth 32 and gums 34. The three-dimensional model may further include surface images of the bone structure, lips, and other soft facial tissues. The generation of the three-dimensional digital model of the actual orthodontic structure 28 is further described in the previously mentioned co-pending patent application having Ser. No. 09/560,584.

Figure 3:
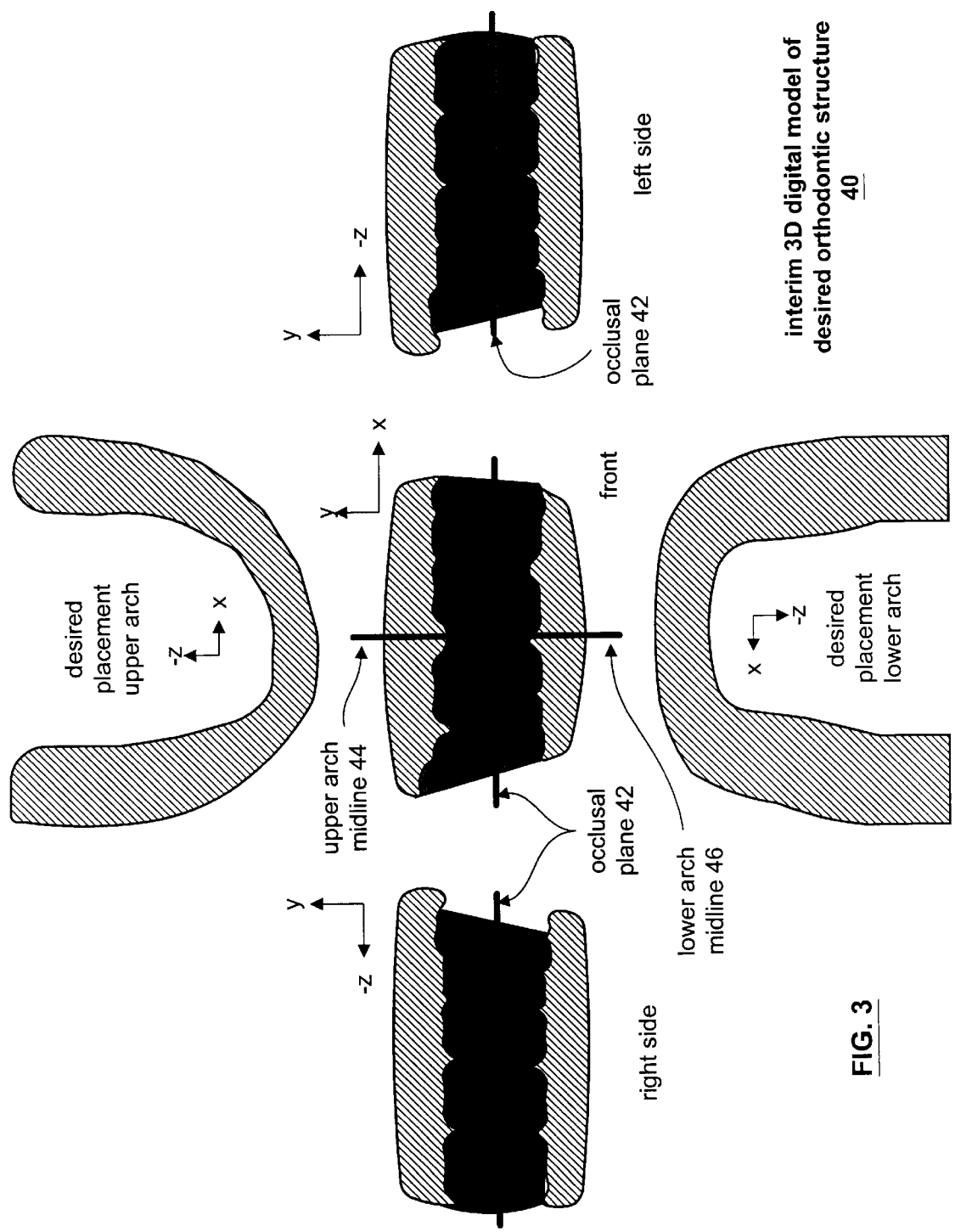
FIG. 3 illustrates a graphical representation of an interim three-dimensional model of a desired orthodontic structure in accordance with the present invention.

FIG. 3 illustrates a graphical diagram of an interim three-dimensional digital model of the desired orthodontic structure 40. In this illustration, the teeth have been removed from the upper and lower gums. In addition, the upper arch and lower arch have been positioned in accordance with an occlusal plane 42. As is known, the occlusal plane 42 defines a plane between the upper arch and the lower arch where, in an ideal orthodontic structure, the upper and lower teeth meet. In addition to aligning the upper and lower arches to the occlusal plane, the upper arch is aligned in accordance with the upper arch midline 44. The lower arch is further aligned in accordance with the lower-arch midline 46. In a desired orthodontic structure, the upper-arch midline 44 is coincident with the lower-arch midline 46. In addition to positioning the upper and lower arches in accordance with the occlusal plane 42 the upper-arch midline 44 and the lower-arch midline 46, the shapes of the upper and lower arches may also be redefined. For example, the upper arch may be reshaped to provide a more ideal arch shape. Similarly, the lower arch may be reshaped to provide a more ideal arch shape. As a further example, the lower arch may be reshaped to better match the upper-arch, or vice-versa. Such modification of the arches, and other aspects of the interim three-dimensional digital model of the desired orthodontic structure 40, is done in the digital domain to enable an orthodontic practitioner to "experiment" with different treatment options. Accordingly, the practitioner may digitally modify the patient's orthodontic structure to obtain a desired appearance and/or function prior to applying any orthodontic apparatus on the patient.

Figure 4:
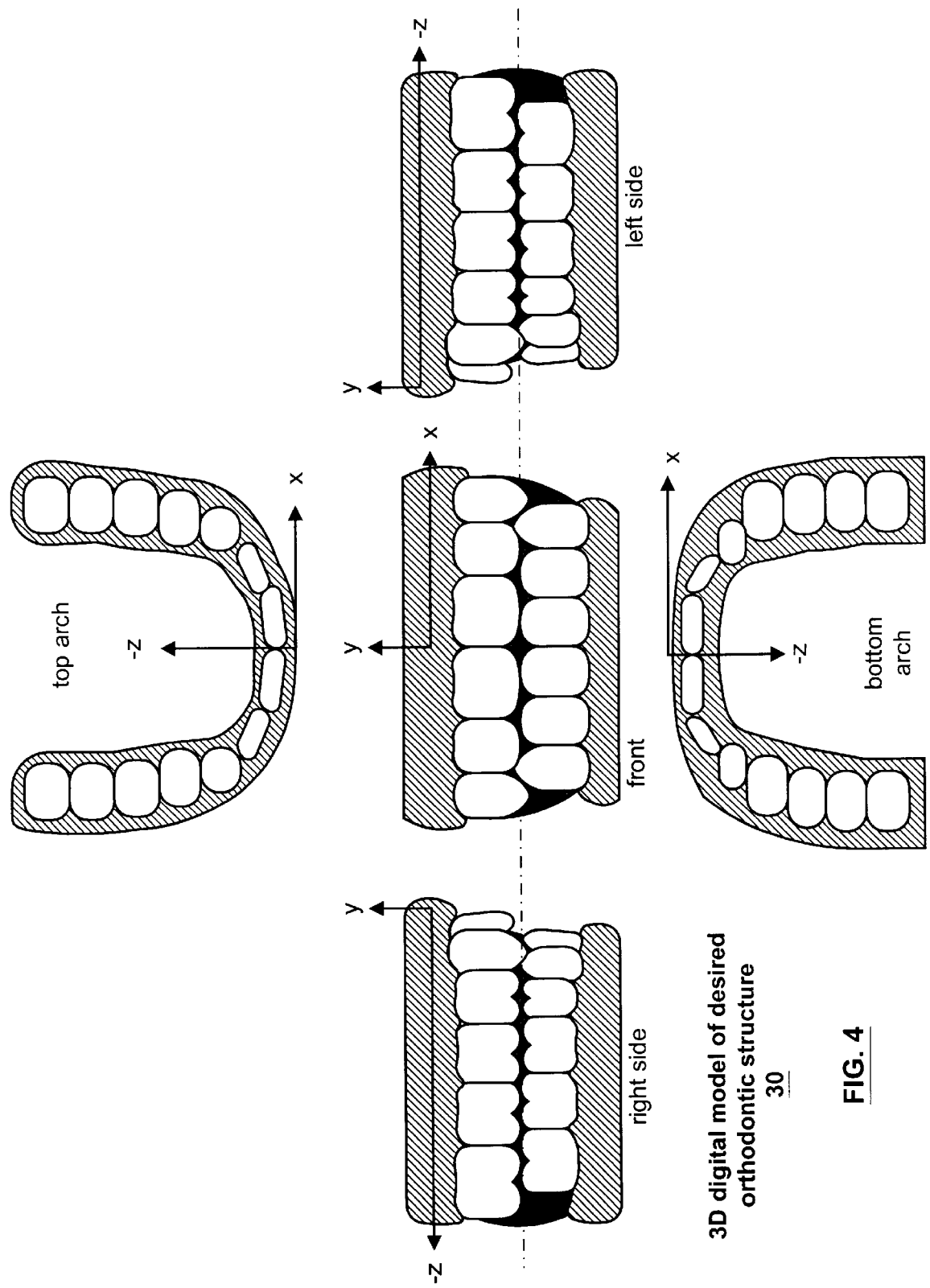
FIG. 4 illustrates a graphical diagram of a three-dimensional digital model of a desired orthodontic structure in accordance with the present invention.

FIG. 4 illustrates a graphical representation of the three-dimensional model of the desired orthodontic structure 30. In this illustration, the teeth have been positioned in the interim three-dimensional digital model of the desired orthodontic structure 40 to be in desired positioning. Accordingly, the upper teeth and lower teeth meet at the occlusal plane 42. In addition, the upper and lower arches are positioned such that the interaction of the upper teeth and lower teeth is functionally appropriate. As shown, in the right and left sides of the desired orthodontic structure 30, the lower molars are offset by approximately half of the distance of the upper molars, such that the function of the teeth is proper. In addition, the lower arch is slightly smaller than the upper-arch such that the upper and lower teeth align with the appropriate function. Note that the positioning of the teeth in the desired orthodontic structure 30 may be done in an automated process, i.e., calculated based on parameters provided to the orthodontic server 14. Alternatively, the teeth may be positioned in an interactive approach wherein a practitioner provides input as to the placement of the teeth. In the interactive approach, the orthodontic server 14 records the inputs and positions the teeth accordingly.

Figure 5:
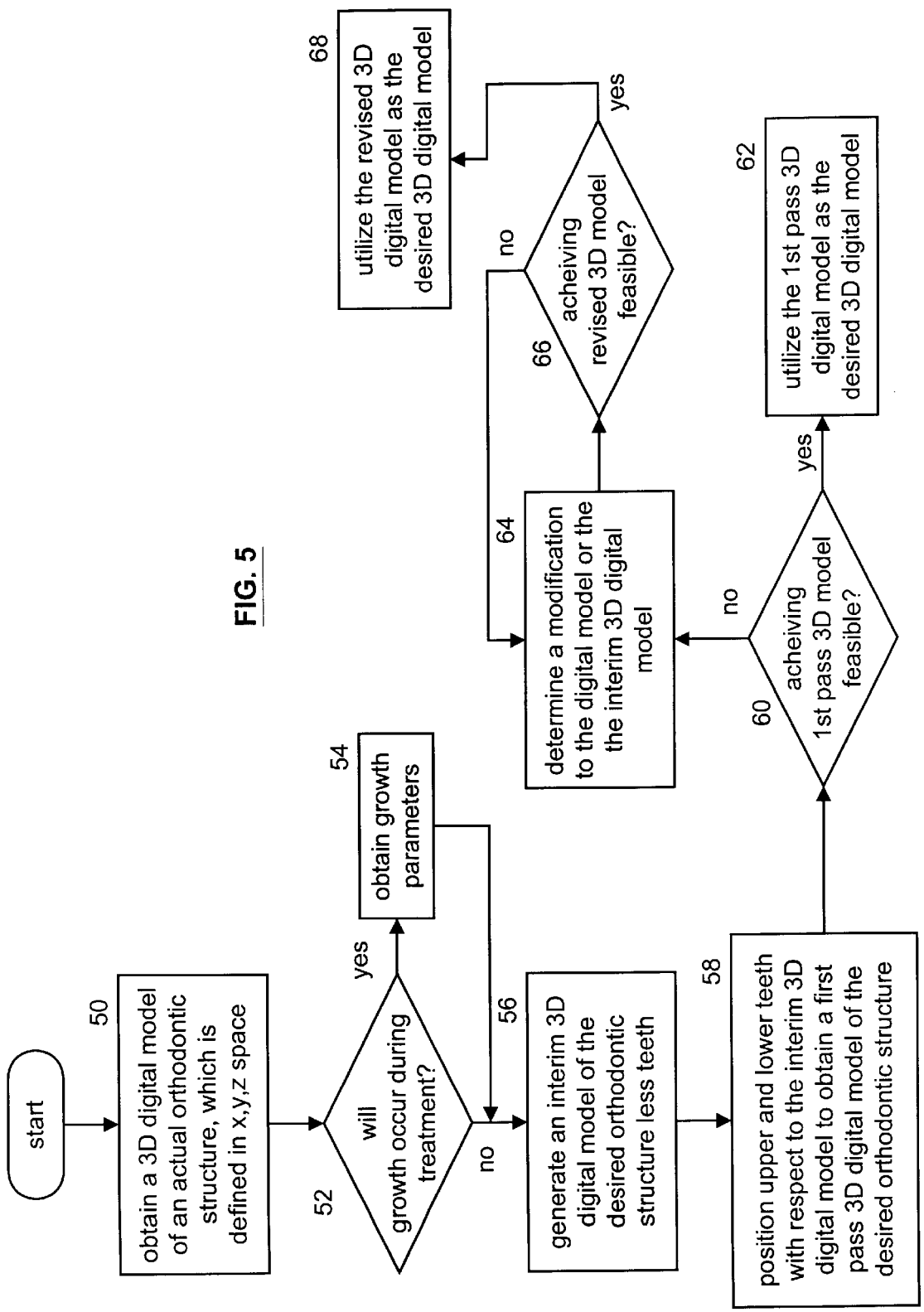
FIG. 5 illustrates a logic diagram of a method for generating a three-dimensional digital model of a desired orthodontic structure in accordance with the present invention.

FIG. 5 illustrates a logic diagram of a method for generating a three-dimensional digital model of a desired orthodontic structure. The process begins at step 50 where a three-dimensional digital model of an actual orthodontic structure is obtained. The three-dimensional digital model of the actual orthodontic structure is defined in x, y, z space. The process then proceeds to step 52 where a determination is made as to whether growth of the orthodontic structure will occur during treatment or whether a new tooth will erupt. If so, the process proceeds to step 54 where growth parameters and/or tooth parameters are obtained from database 28.

Whether growth will occur or not, the process proceeds to step 56. At step 56 an interim three-dimensional digital model of the desired orthodontic structure is generated without teeth. The interim three-dimensional model includes desired placement of the occlusal plane, the upper-arch form, the lower-arch form, an upper-arch midline and/or the lower-arch midline. The process then proceeds to step 58 where the upper and lower teeth are positioned with respect to the interim three-dimensional digital model to obtain a first pass three-dimensional digital model of the desired orthodontic structure. Note that if growth will occur during the treatment, the interim three-dimensional digital model is modified to include the growth aspects. For example, if it is determined during the course of treatment, the orthodontic structure will grow by two percent, the two percent is factored into the interim three-dimensional digital model. In addition, the process may use a primary factor in positioning the upper and lower teeth. The primary factor relates to the desired orthodontic structure and may be soft tissue appearance, dental appearance, dental and/or oral function, stability, and/or hard tissue positioning. As such, if the primary factor is dental appearance, the teeth will be positioned to provide the best appearance, with function and soft tissue appearance being secondary considerations. Of course, it is desirable to produce the ideal orthodontic structure that does not compromise dental appearance, soft tissue appearance, and dental function. In situations where the ideal orthodontic structure cannot be obtained, the primary factor is used to provide the patient with as close to the ideal orthodontic structure as possible.

The positioning of the upper and lower teeth may be done in an automated process, on a tooth by tooth basis, such that the orthodontic server 14 automatically positions the teeth into a desired location in accordance with the primary factor. Alternatively, the positioning of the upper and lower teeth may be done in an interactive approach. For example, an orthodontic practitioner may provide inputs as to the positioning of each of the upper and lower teeth. In this manner, the orthodontic practitioner can place the teeth in the desired positions in accordance with one or more of the primary factors. As such, each tooth is treated as an independent entity for the purposes of ideal placement.

The process then proceeds to step 60 where a determination is made as to whether achieving the first pass three-dimensional digital model is feasible (the determination of feasibility is discussed below with reference to FIGS. 6 and 7). If yes, the process proceeds to step 62 where the first pass three-dimensional digital model is used as the desired three-dimensional model. If, however, achieving the first pass three-dimensional digital model is not feasible, the process proceeds to step 64. At step 64, a modification to the digital model or the interim three-dimensional digital model is determined. Such a modification include changing the position of a tooth, changing the occlusal plane, the upper and lower arch, the midline for the upper and/or lower arch, etc.

The process then proceeds to step 66 where a determination is made as to whether achieving the revised three-dimensional model is feasible. If not, the process reverts to step 64 where another modification is made to the digital model or the interim three-dimensional digital model. Once determining that the revised three-dimensional digital model is feasible, the process proceeds to step 68. At step 68, the revised three-dimensional digital model is used as the desired three-dimensional digital model.

Figure 6:
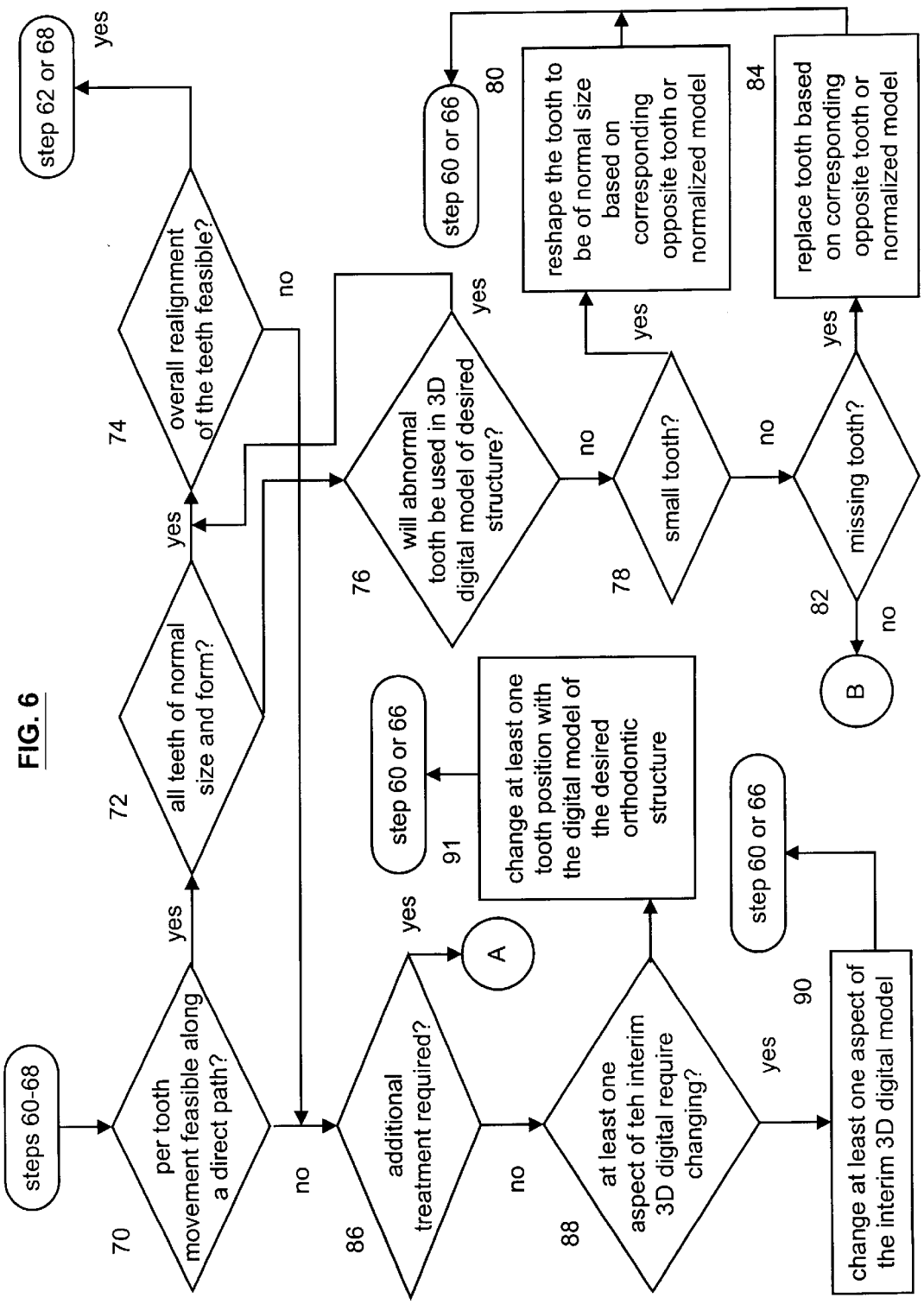
FIGS. 6 and 7 illustrates a logic diagram of the method steps 60 through 68 of FIG. 5.
Figure 7:
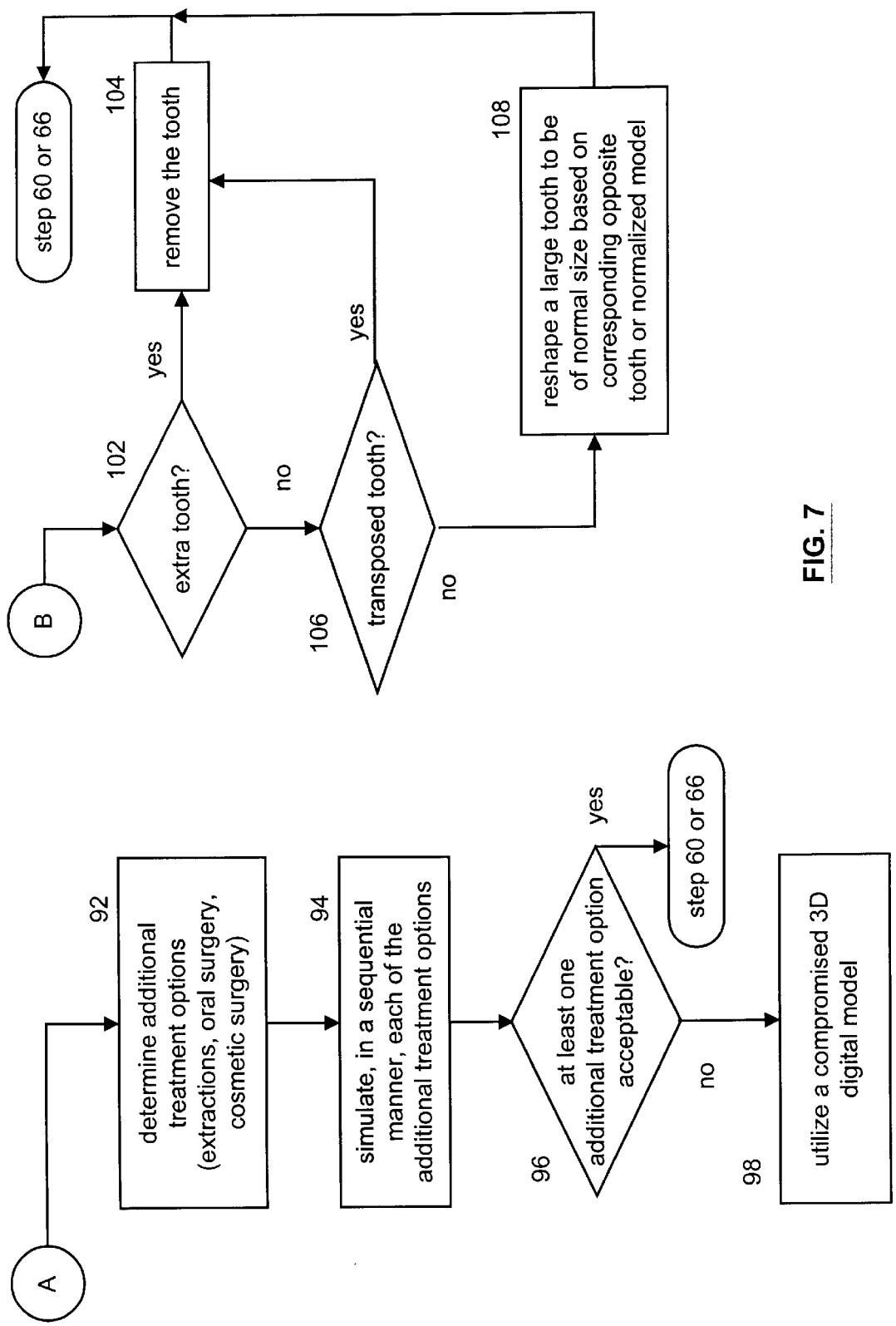

FIGS. 6 and 7 illustrate the operational instructions of steps 60 through 68 in greater detail. The more detailed processing begins at step 70 where a determination is made as to whether per tooth movement is feasible along a direct path and there is sufficient room in the arches to fit all of the teeth. The process for determining the per tooth movement is further described in co-pending patent application, which is hereby incorporated herein by reference, having Ser. No. 09/560,640, entitled METHOD AND APPARATUS FOR SIMULATING TOOTH MOVEMENT FOR AN ORTHODONTIC PATIENT, having a filing date the same as the present patent application, and is assigned to the same assignee as the present patent application.

If the per tooth movement is feasible, the process proceeds to step 72 where a determination is made as to whether all of the teeth are of normal size and form. If the teeth are of normal size and form, the process proceeds to step 74 where a determination is made as to whether the overall realignment of the teeth is feasible. Factors that affect the overall realignment of the teeth include stability, aesthetics, function, occlusal scheme, cooperation of patient with use of extended gear (e.g., head gear, rubber bands etc.), the physical aspects of the patient including the physiological aspects, biological aspects, and anatomy. Further factors include the orientation of the roots, crown positioning, intercuspation fit, treatment time, patient's expectations, and/or costs. If the overall realignment is feasible, the processing is complete and the desired three-dimensional digital model is obtained.

If the per tooth movement is not feasible, or the overall realignment of the teeth is not feasible, the process proceeds to step 86. At step 86, a determination is made as to whether additional treatment is required. If additional treatment is not required, the process proceeds to step 88 where a determination is made as to whether at least one aspect of the interim three-dimensional digital model requires changing. Accordingly, the determination at step 88 is determining whether the occlusal plane needs to be changed, the shape of the upper or lower arch needs to be changed, or the positioning of the upper or lower midline needs to be changed. If so, the process proceeds to step 90 where at least one aspect of the interim digital model is changed. Having done this, the process reverts to step 60 or 66 for further processing.

If, at step 88 it was determined that one aspect of the interim three-dimensional digital model did not require changing, the process proceeds to step 91. At step 91, at least one tooth position is changed within the digital model of the desired orthodontic structure. At this point, the process reverts to step 60 or 66 for further processing. Note that the determination of step 88 may be done in an automated manner based on case histories, patient information, desired results, etc. Alternatively, the determination at step 88 may be done in an interactive process with an orthodontic practitioner. As such, the orthodontic practitioner may determine whether an aspect of the interim three-dimensional digital model requires changing. In addition, the interactive process may be utilized at step 91 to determine the repositioning of the tooth or teeth to obtain the desired three-dimensional model. Note that after step 90 or 91, the feasibility of the revised digital model is tested prior to acceptance.

If, at step 72, it was determined that at least one tooth is not of normal size or form, the process proceeds to step 76. At step 76, a determination is made as to whether the abnormal tooth will be used in the three-dimensional digital model of the desired structure. If so, the process reverts to step 74. If, however, the abnormal tooth will not be used in the three-dimensional digital model, the process proceeds to step 78. At step 78, a determination is made as to whether the abnormality relates to the tooth being too small. If so, the process proceeds to step 80 where the tooth is reshaped to be of normal size based on the corresponding opposite tooth or a normalized model. Having done this, the process reverts to step 60 or 66.

If the tooth is not abnormally small, the process proceeds to step 82 where a determination is made as to whether the abnormality results from a missing tooth. If so, the process proceeds to step 84 where the tooth is replaced in the digital model based on the corresponding opposite tooth or a normalized digital model. Having done this, the process proceeds to step 60 or 66. Note that step 76 through 84 may be done in an automated process by the orthodontic server or in an interactive process between the orthodontic server 14 and an orthodontic practitioner.

If it was determined that the abnormality was not due to a missing tooth, the process proceeds to step 102, which is shown on FIG. 7. At step 102, a determination is made as to whether the abnormal tooth corresponds to an extra tooth. If so, the extra tooth is removed at step 104 from the digital model. Having removed the tooth, the process proceeds to step 66 or 60 of the logic diagram of FIG. 5.

If the abnormal tooth is not an extra tooth, the process proceeds to step 106 where a determination is made as to whether the tooth is transposed. If the tooth is transposed, i.e., not in the appropriate space, the process will proceed to step 104 where the tooth is removed from the digital model. If, however, the abnormal tooth is not transposed, it may be a large tooth. The process then proceeds to step 108 where the large tooth is reshaped to be of normal size based on the corresponding opposite tooth or a normalized model for the tooth. Note that the tooth may be abnormal due to a misalignment between the root and crown, which is known as dilaceration. In this case, an interactive process between the practitioner and the orthodontic server 14 would be conducted to position the tooth as best as possible.

If it was determined that additional treatment were required at step 86, of FIG. 6, the process would proceed to step 92, which is shown on FIG. 7. At step 92, additional treatment options are determined. Such additional treatment options include extraction, oral surgery (e.g., reshape the upper and/or lower arch) and/or cosmetic surgery (e.g., change the lip structure, check bones, chin, etc.). The process proceeds to step 94 where a simulation for each of the additional treatment options is conducted. Such simulation would occur in a sequential order testing one or more of the options. The process then proceeds to step 96 where a determination is made as to whether at least one additional treatment option was acceptable. If so, the process reverts to step 60 or 66 of FIG. 5. If not, the process proceeds to step 98 where a compromised three-dimensional digital model is utilized. Typically, if a compromised three-dimensional digital model will be utilized, the process will determine the least amount of compromise based on the ideal orthodontic structure, the patient's requests, the primary factor, and biological factors of the patient.

Using an iterative method in accordance with the present invention is advantageous over prior methods that were ultimately based upon a single two-dimensional analysis. By using a three-dimensional model in accordance with a specific embodiment of the present invention in conjunction with an iterative process, any factor that effects tooth movement (i.e. brackets, wires, adhesion, physiological changes) can be simulated to determine appropriate treatment changes. Such compensation in treatment is not possible using prior methods which were based upon assumptions from a single model that the tooth movement would progress in a known manner. Therefore, the prior art methods would specify and a single static treatment based upon this assumption.. If any unwanted tooth movement occurred during treatment, the specified treatment would no longer be valid, requiring changes to be made based upon a practitioner's expertise. The present system provides a dynamic system that through the use of periodic feedback, i.e. periodic three-dimensional scanning, can be monitored and adjusted as needed by the system in an efficient manner. As such, unexpected tooth movement, such as occurs when a patient does not cooperate, or through biological changes, can be readily controlled.

The preceding discussion has presented a method and apparatus for generating a three-dimensional digital model of a desired orthodontic structure. By utilizing such a method and apparatus, in an orthodontic treatment system as shown in FIG. 1, the practice of orthodontic treatment may be converted from an art to a science. As one of average skill in the art will appreciate, other embodiments may be derived from the teaching of the present invention without deviating from the scope of the claims.

What is claimed is:

1. A method for generating a three-dimensional digital model of a desired orthodontic structure, the method comprises the steps of:
   a) obtaining a three-dimensional digital model of an actual orthodontic structure, wherein the three-dimensional digital model is defined in x, y, z space;
   b) generating an interim three-dimensional digital model of the desired orthodontic structure less teeth in the defined x, y, z space, wherein the interim three-dimensional digital model includes desired placement of an upper and lower occlusal plane, an upper arch form, a lower arch form, an upper arch midline, and a lower arch midline;
   c) positioning upper and lower teeth with respect to the interim three-dimensional digital model in the defined x, y, z space to obtain a first pass three-dimensional digital model of the desired orthodontic structure;
   d) determining whether achieving the first pass three-dimensional digital model is feasible; and
   e) when achieving the first pass three-dimensional image is feasible, utilizing the first pass three-dimensional digital model as the desired three-dimensional digital model.

2. The method of claim 1, wherein step (b) further comprises:
   determining whether growth will occur during treatment based on patient parameters that are cross referenced to a normalized patient;
   when growth will occur, obtaining growth parameters; and
   generating the interim three-dimensional digital model based on the growth parameters.

3. The method of claim 1, wherein step (c) further comprises:
   determining a primary factor for desired tooth placement within the desired orthodontic structure, wherein the primary factor is at least one of: resulting soft tissue appearance, dental appearance, dental function, stability, and hard tissue positioning.

4. The method of claim 1, wherein step (d) further comprises:
   determining whether per tooth movement is feasible along a direct path for each tooth;
   when the per tooth movement is not feasible, determining whether additional treatment is required;
   when additional treatment is not required, determining whether at least one aspect of the interim three-dimensional digital model requires changing; and
   when the at least one aspect of the interim three-dimensional digital model does not require changing, changing at least one tooth position within the first pass three-dimensional digital model.

5. The method of claim 4 further comprises:
   when the per tooth movement is feasible, determining whether all of the teeth are of normal size and form;
   when all of the teeth are of normal size and form, determining whether overall realignment of the teeth is feasible; and
   when the overall realignment of the teeth is feasible, determining that the first pass three-dimensional digital model is feasible.

6. The method of claim 5 further comprises:
   when at least one tooth is not of normal size or form, determining whether the at least one tooth will be used in the three-dimensional digital model; and
   when the at least one tooth will not be used in the three-dimensional digital model, determining a type of abnormality.

7. The method of claim 6, wherein the type of abnormality is an abnormally small tooth, wherein the method further comprises reshaping the at least one tooth to be of normal size based on at least one of: a corresponding tooth on an opposite side of an arch and a normalized model tooth.

8. The method of claim 6, wherein the type of abnormality is a missing tooth, wherein the method further comprises replacing the missing tooth based on at least one of: a corresponding tooth on an opposite side of an arch and a normalized model tooth.

9. The method of claim 6, wherein the type of abnormality is an extra tooth, wherein the method further comprises removing the at least one tooth.

10. The method of claim 6, wherein the type of abnormality is a transposed tooth, wherein the method further comprises extracting the at least one tooth.

11. The method of claim 6, wherein the type of abnormality is an abnormally large tooth, wherein the method further comprises reducing the size of the at least one tooth based on a corresponding tooth on an opposite side of an arch and a normalized model tooth.

12. The method of claim 4 further comprises:
   when the additional treatment is required, determining additional treatment options;
   simulating, in a sequential manner, each of the additional treatment options;
   when at least one of the additional treatment options is acceptable, utilizing the at least one of the additional treatment options.

13. The method of claim 12 further comprises:
when each of the additional treatment options fails to provide an acceptable option, utilizing a compromised three-dimensional digital model.

14. The method of claim 4 further comprises:
when the at least one aspect of the interim three-dimensional digital model requires changing, changing the at least one aspect of the interim three-dimensional digital model.

15. An apparatus for generating a three-dimensional digital model, the apparatus comprises:
a processing module; and
memory operably coupled to the processing module, wherein the memory includes operational instructions that cause the processing module to: (a) obtain a three-dimensional digital model of an actual orthodontic structure, wherein the three-dimensional digital model is defined in x, y, z space; (b) generate an interim three-dimensional digital model of the desired orthodontic structure less teeth in the defined x, y, z space, wherein the interim three-dimensional digital model includes desired placement of an occlusal plane, an upper arch form, a lower arch form, an upper arch midline, and a lower arch midline; (c) position upper and lower teeth with respect to the interim three-dimensional digital model in the defined x, y, z space to obtain a first pass three-dimensional digital model of the desired orthodontic structure; (d) determine whether achieving the first pass three-dimensional digital model is feasible; and (e) when achieving the first pass three-dimensional image is feasible, utilize the first pass three-dimensional digital model as the desired three-dimensional digital model.

16. The apparatus of claim 15, wherein the memory further comprises operational instructions that cause the processing module to:
determine whether growth will occur during treatment based on patient parameters that are cross referenced to a normalized patient;
when growth will occur, obtain growth parameters; and
generate the interim three-dimensional digital model based on the growth parameters.

17. The apparatus of claim 15, wherein the memory further comprises operational instructions that cause the processing module to:
determine a primary factor for desired tooth placement within the desired orthodontic structure, wherein the primary factor is at least one of: resulting soft tissue appearance, dental appearance, dental function, and hard tissue positioning.

18. The apparatus of claim 15, wherein the memory further comprises operational instructions that cause the processing module to:
determine whether per tooth movement is feasible along a direct path for each tooth;
when the per tooth movement is not feasible, determine whether additional treatment is required;
when additional treatment is not required, determine whether at least one aspect of the interim three-dimensional digital model requires changing; and
when the at least one aspect of the interim three-dimensional digital model does not require changing, change at least one tooth position within the first pass three-dimensional digital model.

19. The apparatus of claim 18, wherein the memory further comprises operational instructions that cause the processing module to:
when the per tooth movement is feasible, determine whether all of the teeth are of normal size and form;
when all of the teeth are of normal size and form, determine whether overall realignment of the teeth is feasible; and
when the overall realignment of the teeth is feasible, determine that the first pass three-dimensional digital model is feasible.

20. The apparatus of claim 19, wherein the memory further comprises operational instructions that cause the processing module to:
when at least one tooth is not of normal size or form, determine whether the at least one tooth will be used in the three-dimensional digital model; and
when the at least one tooth will not be used in the three-dimensional digital model, determine a type of abnormality.

21. The apparatus of claim 20, wherein the memory further comprises operational instructions that cause the processing module to, when the type of abnormality is an abnormally small tooth, reshape the at least one tooth to be of normal size based on at least one of: a corresponding tooth on an opposite side of an arch and a normalized model tooth.

22. The apparatus of claim 20, wherein the memory further comprises operational instructions that cause the processing module to, when the type of abnormality is a missing tooth, replace the missing tooth based on at least one of: a corresponding tooth on an opposite side of an arch and a normalized model tooth.

23. The apparatus of claim 20, wherein the memory further comprises operational instructions that cause the processing module to, when the type of abnormality is an extra tooth, remove the at least one tooth.

24. The apparatus of claim 20, wherein the memory further comprises operational instructions that cause the processing module to, when the type of abnormality is a transposed tooth, extract the at least one tooth.

25. The apparatus of claim 20, wherein the memory further comprises operational instructions that cause the processing module to, when the type of abnormality is an abnormally large tooth, reduce the size of the at least one tooth based on a corresponding tooth on an opposite side of an arch and a normalized model tooth.

26. The apparatus of claim 18, wherein the memory further comprises operational instructions that cause the processing module to: when the additional treatment is required, determine additional treatment options;
simulate, in a sequential manner, each of the additional treatment options;
when at least one of the additional treatment options is acceptable, utilize the at least one of the additional treatment options.

27. The apparatus of claim 26, wherein the memory further comprises operational instructions that cause the processing module to:
when each of the additional treatment options fails to provide an acceptable option, utilize a compromised three-dimensional digital model.

28. The apparatus of claim 18, wherein the memory further comprises operational instructions that cause the processing module to:
when the at least one aspect of the interim three-dimensional digital model requires changing, change the at least one aspect of the interim three-dimensional digital model.

* * * * *